United States Patent
Harris et al.

(10) Patent No.: US 9,445,886 B2
(45) Date of Patent: Sep. 20, 2016

(54) VASCULAR PROSTHESIS

(75) Inventors: Peter Lyon Harris, Liverpool (GB);
Thien Voon How, Liverpool (GB)

(73) Assignee: Bard Peripheral Vascular, Inc.,
Tempe, AZ (US)

( * ) Notice: Subject to any disclaimer, the term of this patent is extended or adjusted under 35 U.S.C. 154(b) by 0 days.

(21) Appl. No.: 10/603,952

(22) Filed: Jun. 25, 2003

(65) Prior Publication Data

US 2004/0064181 A1 Apr. 1, 2004

Related U.S. Application Data (63) Continuation of application No. 09/762,761, filed as application No. PCT/GB98/01418 on May 15, 1998, now Pat. No. 6,589,278.

(30) Foreign Application Priority Data

May 17, 1997 (GB) .................................. 9709967.5

(51) Int. Cl.
*A61F 2/06* (2006.01)
*A61B 17/11* (2006.01)

(52) U.S. Cl.
CPC ........ *A61F 2/064* (2013.01); *A61B 2017/1135* (2013.01); *A61F 2002/068* (2013.01); *A61F 2230/008* (2013.01)

(58) Field of Classification Search
USPC .............................. 623/1.3, 1.31, 1.35, 1.36
See application file for complete search history.

(56) References Cited

U.S. PATENT DOCUMENTS

| | | |
|---|---|---|
| 2,127,903 A | 8/1938 | Bowen |
| 3,196,194 A | 7/1965 | Ely, Jr. et al. |
| 3,492,994 A | 2/1970 | Field |
| 3,683,926 A | 8/1972 | Suzuki |
| 3,713,441 A | 1/1973 | Thomas |
| 3,805,301 A | 4/1974 | Liebig |
| 3,815,608 A | 6/1974 | Spinosa et al. |
| 3,816,919 A | 6/1974 | Portnoy |
| 3,818,511 A * | 6/1974 | Goldberg et al. ............ 623/1.31 |
| 3,825,257 A | 7/1974 | Palmer |
| 3,826,257 A | 7/1974 | Buselmeier |
| 3,853,462 A | 12/1974 | Smith |

(Continued)

FOREIGN PATENT DOCUMENTS

| | | | |
|---|---|---|---|
| EP | 0 269 254 A1 | | 10/1987 |
| GB | 1 508 546 | * | 4/1978 |

(Continued)

OTHER PUBLICATIONS

Advertisement for FEP-Ringed GORE-TEX Vascular Graft, prior to Jun. 21, 1989; one page.*
"Interposition Vein Patches for Vascular Reconstruction", pp. 1-3, J.F. Chester et al.
"The Use of the Vein Cuff and PTFE", Vascular Surgical Techniques, as Atlas, Second Edition, pp. 276-286, Justin H. Miller et al.

(Continued)

*Primary Examiner* — David H Willse
(74) *Attorney, Agent, or Firm* — C.R. Bard Intellectual Property; Buchalter Nemer (57) ABSTRACT

A vascular prosthesis configured for direct connection to an artery. The vascular prosthesis may include a tube of material other than autologous vascular tissue, having an end formation, which is configured for surgical connection to an opening formed in the artery, and a narrower portion prior to commencement of the end formation. The end formation may have an enlarged chamber adapted to induce a concave section in the blood vessel upon attachment thereto.

18 Claims, 4 Drawing Sheets

(56) References Cited

U.S. PATENT DOCUMENTS

| | | | |
|---|---|---|---|
| 3,882,862 A | 5/1975 | Berend | |
| 3,945,052 A | 3/1976 | Liebig | |
| 3,986,828 A | 10/1976 | Hoffman, Jr. et al. | |
| 4,047,252 A | 9/1977 | Liegib et al. | |
| 4,098,571 A | 7/1978 | Miyata et al. | |
| 4,192,312 A | 3/1980 | Wilson | |
| 4,234,535 A | 11/1980 | Okita | |
| 4,279,259 A | 7/1981 | Lee et al. | |
| 4,309,776 A | 1/1982 | Berguer | |
| 4,313,231 A | 2/1982 | Koyamada | |
| 4,321,914 A | 3/1982 | Begovac et al. | |
| 4,345,414 A | 8/1982 | Bornat et al. | |
| 4,354,495 A | 10/1982 | Bodicky | |
| 4,366,819 A | 1/1983 | Kaster | |
| 4,387,516 A | 6/1983 | Laux | |
| 4,416,028 A | 11/1983 | Eriksson et al. | |
| 4,441,215 A | 4/1984 | Kaster | |
| 4,482,516 A | 11/1984 | Bowman et al. | |
| 4,501,263 A | 2/1985 | Harbuck | |
| 4,503,568 A | 3/1985 | Madras | |
| 4,517,687 A | 5/1985 | Liebig et al. | |
| 4,530,113 A | 7/1985 | Matterson | |
| 4,561,129 A | 12/1985 | Arpesella | |
| 4,601,718 A * | 7/1986 | Possis et al. | 623/1.26 |
| 4,630,375 A | 12/1986 | Spolyar | |
| 4,712,551 A * | 12/1987 | Rayhanabad | 604/8 |
| 4,714,421 A | 12/1987 | D'Agostino | |
| 4,728,328 A | 3/1988 | Hughes et al. | |
| 4,743,480 A | 5/1988 | Campbell et al. | |
| 4,807,622 A | 2/1989 | Ohkaka et al. | |
| 4,816,028 A | 3/1989 | Kapadia et al. | |
| 4,840,940 A | 6/1989 | Sottiurai | |
| 4,872,455 A | 10/1989 | Pinchuk et al. | |
| 4,883,453 A | 11/1989 | Berry et al. | |
| 4,909,979 A | 3/1990 | Possis et al. | |
| 4,935,190 A | 6/1990 | Tennerstedt | |
| 4,944,737 A | 7/1990 | Bloom | |
| 4,957,508 A | 9/1990 | Kaneko et al. | |
| 4,957,669 A | 9/1990 | Primm | |
| 5,042,161 A | 8/1991 | Hodge | |
| 5,078,735 A | 1/1992 | Mobin-Uddin | |
| 5,100,422 A | 3/1992 | Berguer et al. | |
| 5,110,526 A | 5/1992 | Hayashi et al. | |
| 5,156,619 A * | 10/1992 | Ehrenfeld | 623/1.31 |
| 5,304,340 A | 4/1994 | Downey | |
| D348,618 S | 7/1994 | Leslie et al. | |
| 5,376,110 A | 12/1994 | Tu et al. | |
| 5,387,236 A | 2/1995 | Noishiki et al. | |
| 5,399,352 A | 3/1995 | Hanson | |
| 5,443,497 A | 8/1995 | Venbrux | |
| 5,456,712 A | 10/1995 | Maginot | |
| 5,456,714 A | 10/1995 | Owen | |
| 5,472,404 A | 12/1995 | Volgushev | |
| 5,476,506 A * | 12/1995 | Lunn | 623/1.28 |
| 5,496,341 A | 3/1996 | Sauer et al. | |
| 5,500,014 A * | 3/1996 | Quijano et al. | 623/1.24 |
| 5,575,817 A | 11/1996 | Martin | |
| 5,591,203 A | 1/1997 | Fahy | |
| 5,653,743 A | 8/1997 | Martin | |
| 5,683,449 A | 11/1997 | Marcade | |
| 5,695,504 A * | 12/1997 | Gifford et al. | 606/153 |
| 5,713,859 A | 2/1998 | Finch, Jr. et al. | |
| 5,723,005 A | 3/1998 | Herrick | |
| 5,752,934 A | 5/1998 | Campbell et al. | |
| 5,755,779 A * | 5/1998 | Horiguchi | 606/157 |
| 5,755,780 A | 5/1998 | Finch, Jr. et al. | |
| 5,782,916 A * | 7/1998 | Pintauro et al. | 623/23.66 |
| 5,814,005 A | 9/1998 | Barra et al. | |
| 5,824,010 A | 10/1998 | McDonald | |
| 5,827,327 A | 10/1998 | McHaney et al. | |
| 5,843,158 A | 12/1998 | Lenker et al. | |
| 5,843,165 A | 12/1998 | Plaia et al. | |
| 5,849,036 A | 12/1998 | Zarate | |
| 5,861,026 A | 1/1999 | Harris et al. | |
| 5,893,886 A | 4/1999 | Zegdi et al. | |
| 5,902,317 A | 5/1999 | Kleshinski et al. | |
| 5,950,320 A | 9/1999 | Dorsey | |
| 5,976,159 A | 11/1999 | Heartport | |
| 5,989,287 A | 11/1999 | Yang et al. | |
| 6,019,788 A * | 2/2000 | Butters et al. | 623/1.35 |
| 6,039,754 A | 3/2000 | Caro | |
| 6,048,362 A | 4/2000 | Berg | |
| 6,056,717 A | 5/2000 | Finch et al. | |
| 6,086,553 A | 7/2000 | Akbik | |
| 6,102,884 A | 8/2000 | Squitieri | |
| 6,136,022 A | 10/2000 | Nunez et al. | |
| 6,187,033 B1 | 2/2001 | Schmitt et al. | |
| 6,190,590 B1 | 2/2001 | Randall et al. | |
| 6,193,746 B1 | 2/2001 | Strecker | |
| 6,203,735 B1 | 3/2001 | Edwin et al. | |
| 6,210,430 B1 | 4/2001 | Solem | |
| 6,221,101 B1 | 4/2001 | Harris et al. | |
| 6,273,912 B1 | 8/2001 | Scholz et al. | |
| 6,302,908 B1 * | 10/2001 | Parodi | 623/1.31 |
| 6,371,981 B1 | 4/2002 | Yang et al. | |
| 6,436,135 B1 | 8/2002 | Goldfarb | |
| 6,458,155 B1 | 10/2002 | Van Nguyen et al. | |
| 6,554,856 B1 | 4/2003 | Doorly et al. | |
| 6,582,409 B1 | 6/2003 | Squitieri | |
| 6,585,762 B1 | 7/2003 | Stanish | |
| 6,589,278 B1 | 7/2003 | Harris et al. | |
| 6,613,087 B1 | 9/2003 | Healy et al. | |
| 6,626,865 B1 | 9/2003 | Prisell | |
| 6,626,939 B1 | 9/2003 | Burnside et al. | |
| 6,746,480 B2 | 6/2004 | Scholz et al. | |
| 6,767,358 B2 | 7/2004 | Leonhardt et al. | |
| 6,821,295 B1 | 11/2004 | Farrar | |
| 6,857,196 B2 | 2/2005 | Dalrymple | |
| 6,858,035 B2 | 2/2005 | Whayne | |
| 7,553,316 B2 | 6/2009 | Scholz et al. | |
| 8,709,069 B2 | 4/2014 | Scholz et al. | |
| 2002/0193872 A1 | 12/2002 | Trout et al. | |
| 2003/0014108 A1 | 1/2003 | Lauren | |
| 2003/0051362 A1 | 3/2003 | Buckman et al. | |
| 2003/0182815 A1 | 10/2003 | Carlson | |
| 2004/0039453 A1 | 2/2004 | Anderson et al. | |
| 2004/0210302 A1 | 10/2004 | Scholz et al. | |
| 2005/0055079 A1 | 3/2005 | Duran | |
| 2005/0272806 A1 | 12/2005 | Falotico et al. | |
| 2006/0030935 A1 | 2/2006 | Scholz et al. | |
| 2006/0210816 A1 | 9/2006 | Finley | |
| 2007/0005128 A1 | 1/2007 | Scholz et al. | |
| 2007/0255400 A1 | 11/2007 | Parravicini et al. | |
| 2010/0280598 A1 | 11/2010 | Fox | |
| 2014/0208913 A1 | 7/2014 | Scholz et al. | |

FOREIGN PATENT DOCUMENTS

| | | |
|---|---|---|
| WO | WO 95/09585 A1 * | 4/1995 |
| WO | 9514442 | 6/1995 |
| WO | WO 95/34255 A1 * | 12/1995 |
| WO | WO 96/00103 | 1/1996 |
| WO | WO 96/09800 A * | 4/1996 |
| WO | WO 97/31591 | 9/1997 |
| WO | WO 98/52495 | 11/1998 |

OTHER PUBLICATIONS

"Improved Technique for Polytetraflouroethylene Bypass Grafting: Long-Term Results Using Anastomotic Vein Patches", The British Journal of Surgery, 1992, vol. 79, Apr. 4, 1992, pp. 348-354, R.S. Taylor et al.

"Polytetraflouroethylene (PTFE) Femorodistal Bypass", Rob & Smith's Operative Surgery/Vascular Surgery Fifth Edition, pp. 330-340, John H. N. Wolfe.

Batson, R.C., M.D. et al.; "Linton Patch Angioplasty", Ann. Surg, Jun. 1984, vol. 199, No. 6, pp. 684-693.

Beard, J.D., et al.; "Haemodynamics of the Interposition Vein Cuff", Br. J. Surg., vol. 73, No. 10, Oct. 1986, 823-825.

Jamieson, et al, "Vascular Surgery", 5th Ed., pp. 330-340 (1994).

Lei, M. PhD et al., "Computational Design of a Bypass Graft That Minimizes Wall Shear Stree Gradients in the Region of the Distal Anastomosis", Journal of Vascular Surgery, Apr. 1997, vol. 25, No. 4, pp. 637-646.

(56) References Cited

OTHER PUBLICATIONS

Loh, A. et al., "PTFE Bypass Grafting to Isolated Popliteal Segments in Critical Limb Ischaemia", Eur J Vasc Surg, vol. 7, pp. 26-30, Jan. 1993.
Taylor, R.S. et al., "Improved Technique for Polytetrafluoroethylene Bypass Grafting: Long-Term Results Using Anastomotic Vein Patches", Br J Surg, vol. 79, pp. 348-354, Apr. 1992.
Tyrrell, M.R. et al, "New Prosthetic Venous Collar Anastomotic Technique: Combining the Best of Other Procedures", Br J Surg, vol. 78, pp. 1016-1017, Aug. 1991.
"Beneficial Effects of Banding on Venous Intimal-Medial Hyperplasia in Arteriovenous Loop Grafts"; Aug. 1989; The American Journal of Surgery, vol. 158; pp. 87-94, Fillinger et al.
"Effect of carotid artery geometry on the magnitude and distribution of wall shear stress gradients"; Apr. 1996; Journal of Vascular Surgery, vol. 23, No. 4; pp. 667-678, Wells et al.
"Flow Disturbance at the Distal End-to-Side Anastomosis"; Nov. 1980; Arch Surg, vol. 115; pp. 1280-1284, Crawshaw et al.
"Graft Geometry and Venous Intimal-Medial Hyperplasia in Arteriovenous Loop Grafts"; Apr. 1990; Journal of Vascular Surgery, vol. 11, No. 4; pp. 556-566, Fillinger et al.
"Mechanical factors predisposing to intimal hyperplasia and medial thickening in autogenous vein grafts"; Mar. 1989; Surgery, vol. 105, No. 3; pp. 393-400, Dobrin et al.
Bard Peripheral Vascular, Inc., 'Venaflo Vascular Grafts Information for Use", Rev. 2, 10/104, 2004.
Bard Peripheral Vascular, Inc.; "Hemodynamics and Cuff Technology", 2005.
Da Silva, A.F. et al, "Stable Vortices Within Vein Cuffs Inhibit Anastomotic Myointimal Hyperplasia", Eur J Vase Sura, vol. 14, pp. 157-163, 1997.
EP 98921634.6 filed May 15, 2008 Office Action dated May 5, 2004.
EP 98921634.6 filed May 15, 2008 Office Action dated Oct. 10, 2005.
Escobar, Francisco S. III et al, "Comparison of a New Hooded Graft With a Conventional ePTFE Graft: A Preliminary Study", Vascular Access for Hemodialysis VI, pp. 205-212, 1999.
Fisher, R.K, et al, "Harnessing Haemodynamic Forces for the Suppression of Anastomotic Intimal Hyperplasia: the Rationale for Precuffed Grafts", Eur J Vase Endovasc Surg, vol. 21, pp. 520-528, 2001.
Gagne, P. J. et al, "The Effect of a Venous Anastomosis Tyrell Vein Collar on the Primary Patency of Arteriovenous Grafts in Patients Undergoing Hemodialysis", J Vase Surg, vol. 32, No. 6, pp. 1149-1154, 2000.
Green, R. M. et al, "Prosthetic Above-Knee Femoropopliteal Bypass Grafting: Five-Year Results of a Randomized Trial", J Vasc Surg, vol. 31, No. 3, pp. 417-425, Mar. 2000.
Harris, Peter et al, "Haemodynamics of Cuffed Arterial Anastomoses", Critical Ischaemia, vol. 9, No. 1, pp. 20-26, 1999.
How, T. V. et al, "Interposition Vein Cuff Anastomosis Alters Wall Shear Stress Distribution in the Recipient Artery", J Vasc Surg, vol. 31, No. 5, pp. 1008-1017, May 2000.
Impra, Inc, "Suturing Technique for Venaflo ePTFE Vascular Graft & Venaflo Graft with Carbon", 1998.
Impra, Inc, "Tunneling Technique for Venaflo ePTFE Vascular Graft & Venaflo Graft with Carbon", 1999.
JP 2006-303732 Office Action dated Jun. 2, 2009. pp. 5-8 (translation).
Krueger et al, "Importance of Correct Trimming of Venaflo Grafts Proven by CFD", 4th International Congress of the Vascular Access Society, Berlin, Germany, May 25, 2005.
Lemson, M.S. et al, "Effects of a Venous Cuff at the Venous Anastomosis of Polytetrafluoroethylene Grafts for Femodialysis Vascular Access", J Vasc Surg, vol. 32, No. 6, pp. 1155-1163, Dec. 2000.

Nyberg et al, "Preliminary Experience with a Cuffed ePTFE Graft for Hemodialysis Vascular Access", Asaio Journel, vol. 47, No. 4, pp. 333-337, Jul./Aug. 2001.
Panneton, J. M., MD., "Multicenter Randomized Prospective Trial Comparing a Pre-Cuffed Polytetrafluoroethylene Graft to a Vein Cuffed Polytetrafluoroethylene Graft for Infragenicular Arterial Bypass", Ann Vasc Sura, vol. 18, pp. 199-206, Mar. 15, 2004.
PCT/GB1998/001418 filed May 15, 1998 International Preliminary Examination Report dated Aug. 25, 1999.
PCT/GB1998/001418 filed May 15, 1998 International Search Report dated Sep. 2, 1998.
PCT/GB1998/001418 filed May 15, 1998 Written Opinion dated Sep. 2, 1998.
PCT/US2008/088312 filed Dec. 24, 2008 Search Report dated Feb. 13, 2009.
PCT/US2008/088312 filed Dec. 24, 2008 Written Opinion dated Feb. 13, 2009.
Scholz, Hans M.D. et al, "Five Years' Experience With an Arteriovenous Patch Prosthesis as Access for Hemodialysis", Vascular Access for Hemodialysis VI, pp. 241-254, 1999.
Sivanesan, S. et al, "Flow Patterns in the Radiocephalic Arteriovenous Fistular: An In Intro Study", J Biomech, vol. 32, pp. 915-925, 1999.
Sorom, AJ. et al, "Prospective, Randomized Evaluation of a Cuffed Expanded Polytetrafluoroethylene Graft for Hemodialysis Vascular Access", Surgery, vol. 132, No. 2, Aug. 2002.
Stonebridge, P.A. et al, "Randomized Trial Comparing Infrainguinal Polytetrafluoroethylene Bypass Grafting With and Without Vein Interpostion Cuff at the Distal Anastomosis", J Vase Sur, vol. 26, No. 4, pp. 543-550, Oct. 1997.
U.S. Appl. No. 10/842,582, filed May 10, 2004 Final Office Action dated Dec. 31, 2008.
U.S. Appl. No. 10/842,582 filed May 10, 2004 Non-Final Office Action dated Jul. 5, 2007.
U.S. Appl. No. 10/842,582 filed May 10, 2004 Non-Final Office Action dated Nov. 16, 2007.
U.S. Appl. No. 11/239,416, filed Sep. 30, 2005 Final Office Action dated Mar. 25, 2010.
U.S. Appl. No. 11/239,416, filed Sep. 30, 2005 Non-Final Office Action dated Sep. 18, 2009.
U.S. Appl. No. 11/408,330, filed Apr. 21, 2006 Advisory Action dated Nov. 23, 2010.
U.S. Appl. No. 11/408,330, filed Apr. 21, 2006 Final Office Action dated Oct. 17, 2012.
U.S. Appl. No. 11/408,330, filed Apr. 21, 2006 Final Office Action dated Sep. 14, 2010.
U.S. Appl. No. 11/408,330, filed Apr. 21, 2006 Non-Final Office Action dated Mar. 24, 2010.
U.S. Appl. No. 11/408,330, filed Apr. 21, 2006 Non-Final Office Action dated Mar. 29, 2012.
U.S. Appl. No. 11/408,330, filed Apr. 21, 2006 Non-Final Office Action dated Sep. 28, 2011.
U.S. Appl. No. 12/810,822, filed Jun. 25, 2010 Final Office Action dated Sep. 28, 2012.
U.S. Appl. No. 12/810,822, filed Jun. 25, 2010 Non-Final Office Action dated Apr. 13, 2012.
U.S. Appl. No. 11/239,416, filed Sep. 30, 2005 Final Office Action dated Dec. 5, 2013.
U.S. Appl. No. 11/239,416, filed Sep. 30, 2005 Non-Final Office Action dated Jun. 7, 2013.
U.S. Appl. No. 11/408,330, filed Apr. 21, 2006 Non-Final Office Action dated Jun. 28, 2013.
U.S. Appl. No. 11/239,416, filed Sep. 30, 2005 Advisory Action dated Feb. 13, 2014.
U.S. Appl. No. 11/239,416, filed Sep. 30, 2005 Non-Final Office Action dated Apr. 11, 2014.
U.S. Appl. No. 11/239,416, filed Sep. 30, 2005 Final Office Action dated Oct. 24, 2014.

* cited by examiner

VASCULAR PROSTHESIS

CROSS-REFERENCE TO RELATED APPLICATIONS

This application is a continuation of application Ser. No. 09/762,761, filed Oct. 5, 2001, now U.S. Pat. No. 6,589,278, which was the National Stage of International Application No. PCT/GB98/01418, filed May 15, 1998, claiming priority to United Kingdom Application No. GB 9709967.5, filed May 17, 1997. This application expressly incorporates by reference the entirety of each of the above-mentioned applications as if fully set forth herein.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

By-passes to save limbs may be required to have a relatively long length, such as the distance from the groin to below the knee, and may be required to attach to arteries that may be as small as 1 mm to 5 mm in diameter. Where patients have no other veins that can be used, as is often the case with patients having relevant serious conditions, the only positive alternative is to use prosthetic grafts of synthetic materials, for example flexible tubes of polytetrafluoroethylene (PTFE). Simple direct end connections or anastomosis of prosthetic graft tubes (usually run at an acute angle or more or less parallel with the artery and end cut at an angle) to side apertures in arteries, perhaps particularly arteries substantially less than 5 mm in diameter, has unfortunately been followed by formation of fibrous intimal hyperplasia, which leads to serious blood flow reduction and even stoppage. The fibrous intimal hyperplasia occurs in regions within and around the graft connection, where there is little or no shear stress between the blood flow and the graft and arterial walls.

It is known to use a small piece of natural vein to make a short cuff known as the Miller cuff, that is joined by surgical stitching to and between the artery opening and the end of the prosthetic graft tube. Improved success rates for indirect prosthesis-to-vein-to-artery connection, compared with direct prosthesis-to-artery, have involved reduced adverse effect from intimal hyperplasia. Contributory factors, for cuff type and other prosthesis types, have been considered and postulated as including reducing tendencies to turbulence of blood flow, and/or optimizing approximation to laminar blood flow, and/or for suppleness of the natural vein parts to aid absorption or cushioning blood pulsing. These factors have further been seen particularly as contributing to avoiding or minimizing occurrence of artery wall shear stress. However, fibrous intimal hyperplasia still occurs with the so called Miller cuff because regions of flow separation and low shear stress still occur within the cuff.

U.S. Pat. No. 5,156,619 discloses a vascular prosthesis comprising a tube of material other than autologous vascular tissue, the tube having an enlarged end formation for surgical connection direct to an opening formed in an artery, the formation having a heel and a toe at opposite ends of a first longer diameter parallel to the axis of the tube and a second shorter transverse diameter. WO 97/31591 discloses a flanged graft for end-to-side anastomosis grafting having an integral terminal flanged skirt or cuff, which facilitates an end-to-side anastomosis directly between an artery and the expanded flange bypass graft without need for an intervening venous collar or venous patch.

It has been proposed to provide a vascular prosthesis comprising a tube of synthetic material having an end formation for surgical connection directly to an opening formed in an artery, the end formation comprising an enlarged chamber serving to promote localized movement of blood having a non-laminar nature with a shear stress inducing relationship to the arterial wall. The term "non-laminar" as used herein is intended to define blood flow other than parallel to arterial walls and, in particular, includes localized laminar movement of blood having significant secondary components. The proposed enlarged chamber has a convex outer wall. Further experimentation, however, has revealed that this type of vascular prosthesis, while representing an improvement on the aforementioned Miller cuff may still not be ideal for certain applications.

Therefore, it is an object of the present invention is to provide an improved vascular prosthesis for use in vascular surgery.

BRIEF SUMMARY OF THE INVENTION

According to the present invention there is provided a vascular prosthesis comprising a tube of material other than autologous vascular tissue, said tube having an end formation for surgical connection direct to an opening formed in an artery, said formation comprising an enlarged chamber having a heel and a toe at opposite ends of a first longer diameter parallel to the axis of the tube and a second shorter transverse diameter, characterized in that a transition between the tube and the toe is outwardly initially convex before a final concave portion, whereby said enlarged chamber serves to promote localized movement of blood having a non-laminar nature with shear stress inducing relationship to receiving arterial wall.

The heel of the enlarged chamber is formed at one end of the longer diameter, and the transition between the tube and the heel is preferably generally concave. Transition between the tube and opposite ends of the shorter diameter is preferably outwardly convex. It is also preferable that the tube have a narrower portion prior to transition to the enlarged chamber. It is believed that such narrowing of the tube will increase blood velocity entering the enlarged chamber of the prosthesis and hence increase shear stress in that region. The grafts of the invention are preferably made of plastics material, especially polytetrafluoroethylene (PTFE).

The vascular prosthesis of the invention is intended to promote vertical blood flow in the region of its arterial connection in order to reduce or eliminate regions of low shear stress and regions of long residence times where blood elements can accumulate in the region of the graft connection. Separation of flowing blood from the inner wall of the tube near its enlarged chamber, and associated with non-laminar flow, is preferably such as to produce a swirling action that may include locally circulatory or re-circulatory movement of blood, further preferably in the nature of or including a vortex action. Such blood flow separation will usually occur directly at, as well as adjacent to, preferred acute angling of the prosthesis tube for its direct connection to the artery, which would be at least partially within the enlarged chamber. A preferred end chamber of the prosthesis tube of the invention is an enlargement which produces blood flow characteristics therein that result in an increase in wall shear stress.

Desired non-laminar blood flow promotion is preferably effective only in phases of cycles of blood-flow pulsing, which phases preferably alternate with other phases of more laminar flow sufficient to assist flow of all blood into the artery away from that end of the prosthesis. The pulsed nature of normal blood flow involved successive time-spaced rises in pressure. Each pressure rise preferably causes both an initial relatively smooth or laminar blood flow in and out of the prosthesis-to-artery connection and a later transition into desired non-blood laminar movement. The preferred non-laminar vortex type movement preferably collapses before the next pressure rise.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
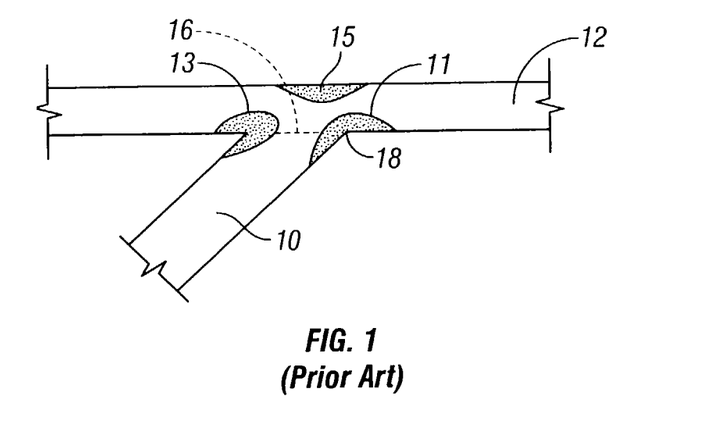
FIG. 1 is a sectional line diagram useful for explaining problems arising from simple direct connection or anastomoses of a prosthetic graft tube of synthetic material to an opening made in an artery.
Figure 2:
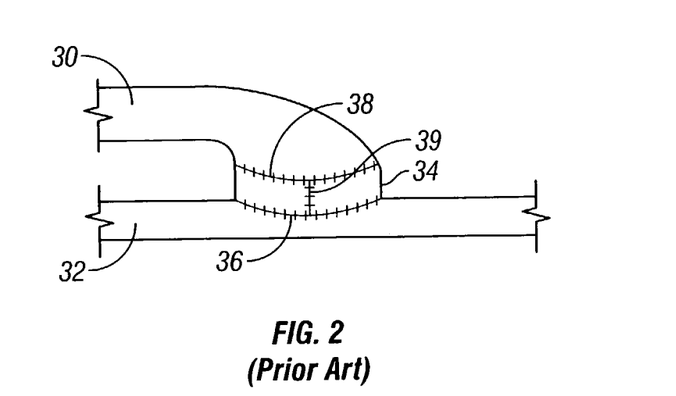
FIG. 2 shows use of a veinous cuff interposed between a prosthetic graft tube and an artery.
Figure 3:
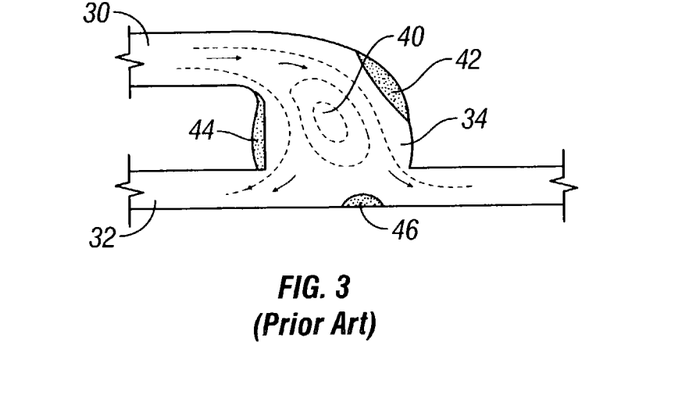
FIG. 3 is a section through the graft of FIG. 2 showing typical blood flow therethrough.
Figure 4:
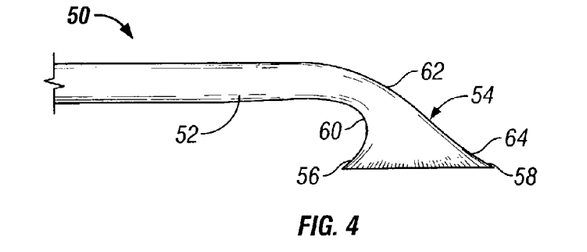
FIG. 4 is a side view of a first prosthetic graft of the invention.
Figure 5:
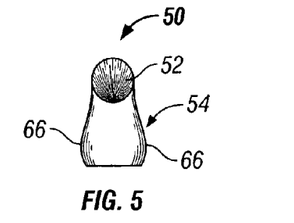
FIG. 5 is a rear view of the graft of FIG. 4.
Figure 6:
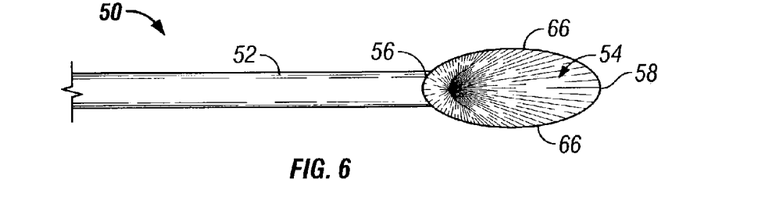
FIG. 6 is a view from below of the graft of FIG. 4.
Figure 7:
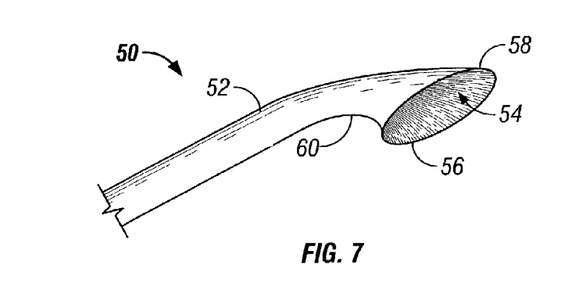
FIG. 7 is a perspective view of the graft of FIG. 4.
Figure 8:
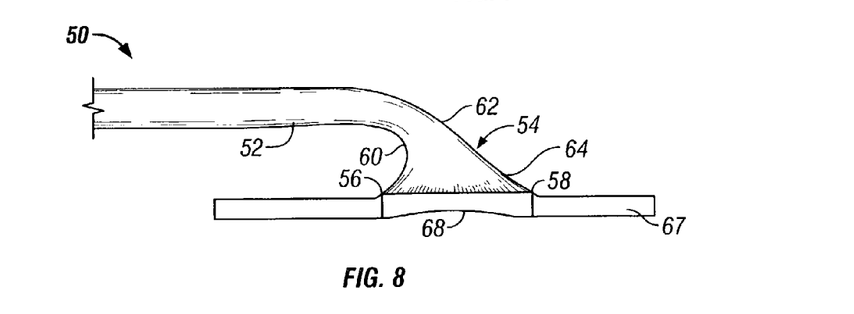
FIG. 8 shows the graft of FIGS. 4 to 7 connected to an artery.
Figure 9:
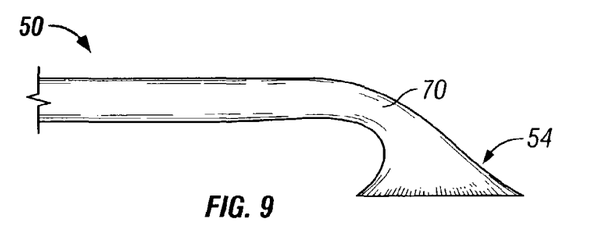
FIG. 9 is a side view of a second prosthetic graft of the invention.
Figure 10:
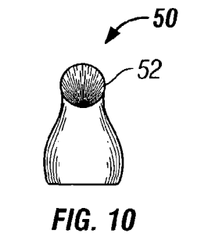
FIG. 10 is a rear view of the graft of FIG. 9.
Figure 11:
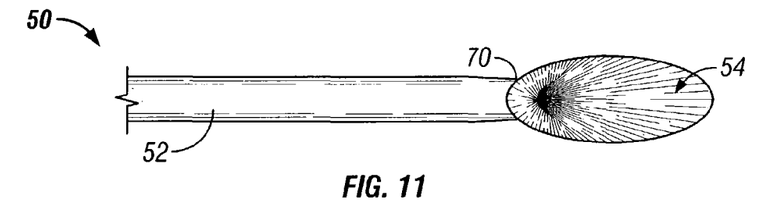
FIG. 11 is a view from below of the graft of FIG. 9.
Figure 12:
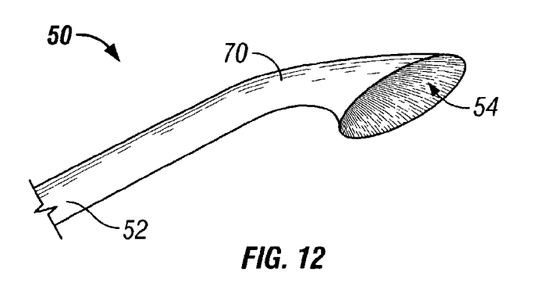
FIG. 12 is a perspective view of the graft of FIG. 9.
Figure 13:
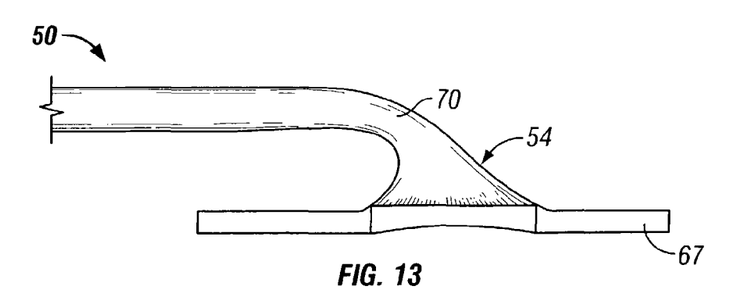
FIG. 13 shows the graft of FIGS. 9 to 12.

In the drawings, prior art devices are depicted in FIGS. 1-3. Referring first to FIG. 1, artery 12 has an opening made by an incision at 16. Prosthetic graft tube 10 of synthetic material (for which PTFE, most usually expanded PTFE (ePTFE), is widely used in practice) is run at an acute angle or more or less parallel to the artery 12. Tube 10 is indicated cut to an angled end 18 that is end to edge sewn into the opening 16. Unfortunately, there is a tendency for myointimal-hyperplasia to occur later in the receiving artery 12 (see indicated development of fibrous or scare-like tissue in the toe and heel positions 11 and 13, respectively), and also at plate position 15 opposite the opening 16. This development can seriously reduce the very blood flow that it is the object of the procedure to improve. Indeed, this condition all too often progresses to complete blockage of such blood flow. These problems are pronounced as the size of the receiving artery 12 decreases, which can be as small as 1 to 5 mm for the type of distal by-passes often needed, such as from the groin to beyond the knee as is frequently necessary to save a patient's lower leg.

FIGS. 2 and 3 illustrate the Miller cuff, aimed at reducing such problems by using a short length of another vein, usually from still usable parts of the saphenous vein that would be used in its entirety if serviceable. This short length of autologous vein, typically 2 to 3 mm in diameter, is removed and opened along its length, then sutured first to an opening 36 of the artery 32 and end-to-end to itself at 39. The completed cuff 34 is trimmed and anastomoses completed at 38 to normally wider prosthetic graft tube 30. The graft tube 30 is typically made of PTFE and is at least 4 mm, preferably 6 mm if not more, in diameter. Improvement in terms of reducing development of intimal hyperplasia was originally, and has since consistently been, attributed to the autologous vein-to-artery junction. The suppleness of the veinous tissue may also have contributed to this improvement by assisting absorption of pressure pulsing and reducing shear wall stress in the receiving artery. Wall shear stress was assumed and reported as being the major causative factor in development of intimal hyperplasia. This procedure has become popular and has been the subject of considerable development, including similar use in interconnected small arteries.

Typical blood flow through the Miller cuff is shown in FIG. 3. A vortex 40 is formed to increase shear stress; however at opposite sides of the cuff, low shear stress regions 42, 44 develop where accumulation of deposits can form, resulting in intimal hyperplasia. Furthermore, where flow separates at the arterial wall opposite the cuff, a low shear stress region 46 also develops where intimal hyperplasia is possible.

Figure 14:
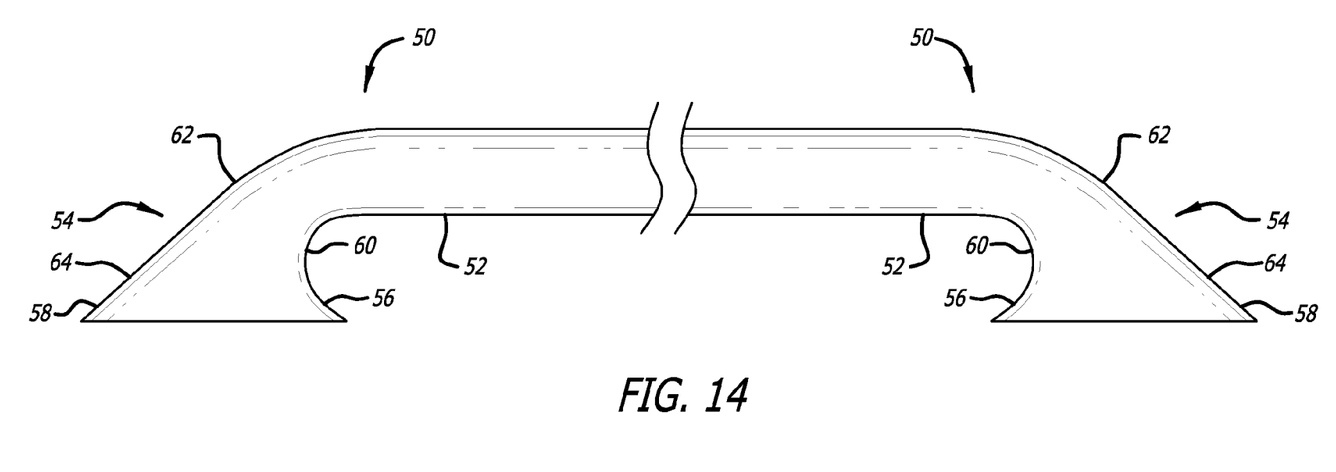
FIG. 14 illustrates a graft with a first and second end formation.

Turning to FIGS. 4 to 8 of the accompanying drawings, a first vascular prosthetic graft 50 according to the invention is ideally made of polytetrafluoroethylene. The graft has a tubular part 52 of any desired length according to the length of the by-pass to be made using the graft and an enlargement 54 at one or both ends of the tube 52 (only one is shown in FIGS. 4 to 8, but FIG. 14 shows an enlargement 54 at both ends of the tube 52). The enlargement 54 has an open end of a generally oval cross-section forming a heel 56 and a toe 58 at opposite ends of the larger diameter of the open end. There is a generally outwardly concave transition 60 between the tube 52 and the heel 56 and between the tube 52 and the toe 58 a firstly convex 62 and a final concave 64 transition. Sides 66 of the enlargement 54 at opposite ends of the shorter diameter of the open end are generally outwardly convex.

The plane of the open end of the enlargement 54 and of the tube 52 are generally parallel but it should be noted that prosthetic grafts having different separations thereof may be made for use in different situations. It should be further noted that prosthetic grafts having open ends of varying longer diameters may be produced. Furthermore, the degree of curvature either to the heel or the toe may be varied from graft to graft, in order to alter blood flow characteristics through the graft connection. The prosthetic graft 50 is in practice connected to an artery by forming a slit in a side of an artery 67, opening out the slit and stitching the open end of the graft to the sides of the slit. It is to be noted that such connection of the graft causes the artery to have a concave underside opposite the graft as can be seen at 68 in FIG. 8 of the drawings. The length of the open end of the graft will probably be in the order of 14 to 36 mm and the width of the open end is unlikely to be less than 6 mm and probably not greater than 14 mm.

FIGS. 9 to 13 illustrate a variation on the prosthetic graft of the present embodiment. Like parts have been numbered similarly and only the main difference between them will now be described. In order to increase the velocity of blood flow through the graft connection to an artery, the tube 52 of the graft includes a narrower portion 70 prior to commencement of the enlargement.

The present invention has been described above in terms of certain preferred embodiments so that an understanding of the present invention can be conveyed. However, there are many alternative arrangements not specifically described herein but with which the present invention is applicable. Although specific features have been provided, the device of the present invention would equally be embodied by other configurations not specifically recited herein. The scope of the present invention should therefore not be limited by the embodiments illustrated, but rather it should be understood that the present invention has wide applicability with respect to vascular prostheses generally. All modifications, variations, or equivalent elements and implementations that are within the scope of the appended claims should therefore be considered within the scope of the invention.

What is claimed as new and desired to be protected by Letters Patent of the United States is:

1. A vascular prosthesis comprising:
a generally tubular portion that defines a blood-flow lumen and that has a luminal surface that contacts blood flowing through the lumen, and an abluminal surface that does not contact blood flowing through the lumen, wherein the luminal surface comprises a material other than vascular tissue,
the tubular portion having
an end formation having a first diameter that tapers to a smaller second diameter adjacent an end of the tubular portion,
the end formation defining an enlarged chamber that terminates at an open end of the vascular prosthesis to define an opening,
the opening having a non-circular perimeter outlining a cross-sectional area larger than a cross-sectional area of the tubular portion at the first diameter,
the enlarged chamber comprises a first diameter parallel to an axis of the tubular portion and a second diameter transverse to the axis of the tubular portion, wherein the enlarged chamber first diameter is longer than the enlarged chamber second diameter, the enlarged chamber first diameter corresponding to a heel and a toe of the end formation, wherein a transition between the tubular portion and the toe is inwardly initially concave before a final inwardly convex portion.

2. The vascular prosthesis of claim 1, wherein the enlarged chamber is configured to promote localized movement of blood having a non-laminar nature with a shear stress inducing relationship to a wall of the blood vessel.

3. The vascular prosthesis of claim 1, wherein a transition between the tubular portion and the heel is generally inwardly convex.

4. The vascular prosthesis of claim 1, wherein portions of the end formation corresponding to opposing ends of the enlarged chamber second diameter are generally outwardly convex.

5. The vascular prosthesis of claim 1, wherein the enlarged chamber first diameter is between approximately 14 and 36 mm and the enlarged chamber second diameter is no greater than approximately 14 mm.

6. The vascular prosthesis of claim 1, wherein the tubular portion and end formation comprise a polytetrafluoroethylene material.

7. The vascular prosthesis of claim 1, wherein the luminal surface consists essentially of a material other than vascular tissue.

8. The vascular prosthesis of claim 7, wherein the luminal surface consists of a material other than vascular tissue.

9. A vascular prosthesis comprising:
a generally tubular portion that defines a blood-flow lumen and that has a luminal surface that contacts blood flowing through the lumen, and an abluminal surface that does not contact blood flowing through the lumen, wherein the luminal surface comprises a material other than vascular tissue,
the tubular portion having
a first end formation having a first diameter that tapers to a smaller second diameter adjacent an end of the tubular portion,
a second end formation,
the first end formation defining an enlarged chamber that terminates at an open end of the vascular prosthesis to define an opening,
the opening having a non-circular perimeter outlining a cross-sectional area larger than a cross-sectional area of the tubular portion at the first diameter,
wherein the second end formation comprises a second enlarged chamber comprising a first diameter parallel to an axis of the tubular portion and a second diameter transverse to the axis of the tubular portion, wherein the second enlarged chamber first diameter is longer than the second enlarged chamber second diameter, the second enlarged chamber first diameter corresponding to a heel and toe of the second end formation, wherein a transition between the tubular portion and the toe is inwardly initially concave before a final inwardly convex portion.

10. The vascular prosthesis of claim 9, wherein a transition between the tubular portion and the heel of the second enlarged chamber is generally inwardly convex.

11. The vascular prosthesis of claim 9, wherein portions of the second end formation corresponding to opposing ends of the second diameter of the second enlarged chamber are generally outwardly convex.

12. The vascular prosthesis of claim 9, further comprising a decreased diameter portion adjacent the second end formation.

13. The vascular prosthesis of claim 9, wherein the tubular portion, first end formation and second end formation comprise a polytetrafluoroethylene material.

14. A vascular prosthesis comprising:
a tube of material having a luminal surface configured for carrying blood to an opening of the tube or for carrying blood from the opening of the tube wherein the luminal surface comprises a material other than vascular tissue having an enlargement positioned at a distal end of the tube, wherein the tube has
   a first diameter portion extending along a majority of the length of the tube and
   a second diameter portion positioned adjacent the enlargement,
    the first diameter portion having a diameter greater than a diameter of the second diameter portion,
the enlargement defining an enlarged chamber that terminates at an open end of the vascular prosthesis to define an opening, the opening having a non-circular perimeter outlining a cross-sectional area larger than a cross-sectional area of the first diameter portion,
the enlargement comprises a first diameter parallel to an axis of the tube and a second diameter transverse to the axis of the tube, wherein the enlargement first diameter is longer than the enlargement second diameter, the enlargement first diameter corresponding to a heel and a toe of the enlargement, wherein a transition between the tube and the toe is inwardly initially concave before a final inwardly convex portion.

15. The vascular prosthesis of claim 14, wherein the open end perimeter has a generally oval shape.

16. The vascular prosthesis of claim 14, wherein the tube and enlargement comprise a polytetrafluoroethylene material.

17. The vascular prosthesis of claim 14, wherein the luminal surface consists essentially of a material other than vascular tissue.

18. The vascular prosthesis of claim 17, wherein the luminal surface consists of a material other than vascular tissue.

* * * * *